(12) United States Patent
Palacios Laloy et al.

(10) Patent No.: US 12,078,690 B2
(45) Date of Patent: Sep. 3, 2024

(54) ARRAY OF MAGNETOMETERS OPERATING IN ZERO FIELD AND ASSOCIATED METHOD FOR CALIBRATING INTER-MAGNETOMETER COUPLINGS

(71) Applicant: COMMISSARIAT A L'ENERGIE ATOMIQUE ET AUX ENERGIES ALTERNATIVES, Paris (FR)

(72) Inventors: Agustin Palacios Laloy, Grenoble (FR); Matthieu Le Prado, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 116 days.

(21) Appl. No.: 17/760,211

(22) PCT Filed: Feb. 3, 2021

(86) PCT No.: PCT/FR2021/050198
§ 371 (c)(1),
(2) Date: Aug. 5, 2022

(87) PCT Pub. No.: WO2021/156568
PCT Pub. Date: Aug. 12, 2021

(65) Prior Publication Data
US 2023/0049365 A1 Feb. 16, 2023

(30) Foreign Application Priority Data
Feb. 7, 2020 (FR) ...................................... 2001234

(51) Int. Cl.
*G01R 33/00* (2006.01)
*A61B 5/242* (2021.01)

(52) U.S. Cl.
CPC .......... *G01R 33/0035* (2013.01); *A61B 5/242* (2021.01); *G01R 33/0094* (2013.01); *A61B 2560/0223* (2013.01)

(58) Field of Classification Search
CPC .................................................. G01R 33/0035
(Continued)

(56) References Cited

U.S. PATENT DOCUMENTS 5,891,031 A * 4/1999 Ohyu ..................... A61B 5/245
600/544
6,538,436 B1 3/2003 Simola et al.
(Continued)

FOREIGN PATENT DOCUMENTS

EP 0 982 597 A2 3/2000
EP 3 299 831 A1 3/2018

OTHER PUBLICATIONS

International Search Report issued May 14, 2021 in PCT/FR2021/050198, filed on Feb. 3, 2021, citing documents 1-2, 15-16 & 26-27 therein, 3 pages.
(Continued)

*Primary Examiner* — Vincent Q Nguyen
(74) *Attorney, Agent, or Firm* — Oblon, McClelland, Maier & Neustadt, L.L.P.

(57) ABSTRACT

A method is provided for determining a coupling between magnetometers of an array of N magnetometers, for example with optical pumping, where each magnetometer includes a field cancellation system capable of being activated to operate the magnetometer in zero field. This method includes a first phase during which one of the N magnetometers is a measuring magnetometer whose field cancellation system is activated and the other N-1 magnetometers have their field cancellation system deactivated. This first phase includes generation by the magnetometers, of a plurality of reference magnetic fields of known amplitudes and distinct directions, the measurement, by the measuring magnetometer, of the ambient magnetic field on a plurality of mea-
(Continued)

surement axes, and determination of coupling coefficients between the measuring magnetometer and each of the N magnetometers from said measurement and said known amplitudes.

10 Claims, 2 Drawing Sheets

(58) Field of Classification Search
USPC .......................................................... 324/202
See application file for complete search history.

(56) References Cited

U.S. PATENT DOCUMENTS

2016/0084925 A1    3/2016   Le Prado et al.
2021/0244330 A1*   8/2021   Shapiro .................. A61B 5/245

OTHER PUBLICATIONS

French Preliminary Search Report issued Oct. 8, 2020 in French Application 20 01234, filed on Feb. 7, 2020, citing documents 1, 15-16 & 26-27 therein, 2 pages (with English Translation of Categories of Cited Documents).

Labyt et al. "Magnetoencephalography With Optically Pumped He-4 Magnetometers at Ambient Temperature", HAL Open Science, 2019, 11 pages.

Osborne et al. "Fully Integrated, Standalone Zero Field Optically Pumped Magnetometer for Biomagnetism", Proceedings of SPIE, vol. 10548, vol. 10524, 2018, 7 pages.

Holmes et al. "A bi-planar coil system for nulling background magnetic fields in scalp mounted magnetoencephalography", NeuroImage 181, 2018, pp. 760-774.

* cited by examiner

ARRAY OF MAGNETOMETERS OPERATING IN ZERO FIELD AND ASSOCIATED METHOD FOR CALIBRATING INTER-MAGNETOMETER COUPLINGS

TECHNICAL FIELD

The field of the invention is that of the imaging of biomagnetic fields, the invention relating more particularly to the arrays of vector magnetometers used in particular in magnetocardiography or magnetoencephalography.

PRIOR ART

The imaging of the magnetic fields generated by different organs of the human body, in particular the heart and the brain, exploits matrices of magnetic sensors (magnetometers) to identify information that is relevant both from the point of view of medical research and that of the diagnosis of different pathologies. Thus, imaging of brain currents allows the study of rapid brain dynamics in a non-invasive manner. It is also used for the preoperative diagnosis of epilepsy, allowing locating epileptogenic areas significantly more accurately than electroencephalography.

In order to carry out a reconstruction of the magnetic field sources (currents circulating in the heart or in the brain for example), it is necessary to have magnetic field measurements along one or different measurement axes as well as the position of the sensors which record them.

Currently, the magnetoencephalography techniques often implement several hundred of the SQUID-type magnetic sensors which have very low intrinsic noise levels but require a cryogenic cooling to operate. Moreover, these imaging techniques are usually practiced inside magnetically shielded enclosures to eliminate external magnetic fields which could disturb the measurements. The size of these enclosures must be large enough to contain the cryogenic container, which results in strong constraints of cost as well as on the architecture of the buildings containing these devices, constraints which are detrimental to their democratisation.

Alternatively, it is possible to use optically pumped magnetometers which have similar intrinsic noise levels, but which do not need to be cooled. Thus the sensors can be disposed closer to the patient's skin, which allows improving the amplitude of the signals as well as the spatial resolution of the measurements. The magnetic shielding can also be reduced, which allows considering a greater diffusion of these techniques in hospitals.

Moreover, the optically pumped magnetometers allow adapting the position of the sensors to the surface of the body of each particular patient. This is an advantage, but requires a calibration of the position of the sensors which must be repeated each time the array is adjusted to the morphology of a new patient. It is therefore important to be able to effectively calibrate the position of the different magnetometers relative to each other, as well as the relative position of this array relative to reference elements positioned on the patient.

Many of the parameters which are sought to locate and calibrate the optically pumped magnetometers (notably gain and linearity) can be stabilised (instead of having to be continuously measured) by closed-loop operation of the magnetometers, that is to say, by retroacting on the coils of each magnetometer to create fields called compensation fields so that each magnetometer operates in a zero total magnetic field (ambient field+compensation field) along its different measurement axes. This closed-loop mode of operation has been used for magnetocardiography and magnetoencephalography measurements as reported, for example, in the following publication: E. Labyt et al., "Magnetoencephalography With Optically Pumped $^4$He Magnetometers at Ambient Temperature", IEEE Transactions on Medical Imaging, vol. 38, no° 1, p. 90-98, jan. 2019.

However, this publication only implements two sensors which are located far enough from each other so as not to be significantly affected by the compensation fields of the other sensor. However, in order to carry out useful medical measurements, it is necessary to implement several tens or even hundreds of these sensors, which makes it necessary to bring them closer to each other. An undesirable effect which then appears is that of a coupling between magnetometers disposed close to each other which are subject to the compensation fields of the others. Thus, it is no longer possible to obtain the value of the pre-existing magnetic field at the operation of the magnetometers from a simple reading of the outputs of the sensors.

However, procedures allow recovering these field values from reading the outputs of the sensors and a matrix which translates the couplings between the different compensation coils and the magnetometers of the array. The patent application EP 3 299 831 A1 thus describes a manner of correcting the couplings in an array of magnetometers operating in a closed loop, as well as a technique for determining the coupling matrix which can be available in two variants: one consists in measuring the couplings with all magnetometers operating in open loop, the other in measuring them with the different magnetometers operating successively in closed loop.

The first of these methods (open-loop calibration) leads to the true coupling coefficients only in the case where the operations are carried out in an environment where the residual fields are almost zero. However, the inventors have been able to experimentally observe that the presence of fields of a few nanotesla leads to the measurement of significant couplings (up to 17%) where the actual couplings are less than 1%. This artefact seems to originate from a second order effect by which the parametric resonance and Hanle effect magnetometers are sensitive not only to the fields along their nominal measurement axes (for example $B_z$ for the z axis), but also with cross terms such as $B_x.B_y$.

Moreover, for the case of parametric resonance magnetometers and as described in the aforementioned patent, the coupling between the coils of a sensor and the sensitive element of another sensor close to the first sensor, also results in an additional drawback. In this magnetometer configuration, radiofrequency fields are applied along one or more axes of the sensor which define the geometric axes along which the different components of the magnetic field are measured. The couplings between two magnetometers whose axes are not oriented in the same manner therefore leads to a modification of their respective measurement axes, which can have a very negative impact on the accuracy of the reconstruction of the magnetic field sources.

DISCLOSURE OF THE INVENTION

The invention aims at proposing a method for determining the couplings between the different magnetometers of an array of optically pumped magnetometers, for example Hanle effect or parametric resonance magnetometers, a method which overcomes the aforementioned drawbacks.

To this end, the invention relates to a method for determining a coupling between magnetometers of an array of N magnetometers where each magnetometer comprises a field cancellation system capable of being activated to operate the magnetometer in zero field. This method comprises a first phase during which the N magnetometers are separated into N−1 magnetometers whose field cancellation system is deactivated and a measuring magnetometer whose field cancellation system is activated. This first phase comprises the following steps:

- generation, by each of the N magnetometers (i.e. the measuring magnetometer and the N61 magnetometers whose field cancellation system is deactivated), of a plurality of reference magnetic fields of known amplitudes and distinct directions,
- measurement, by the measuring magnetometer, of the ambient magnetic field on a plurality of measurement axes;
- determination of coupling coefficients between the measuring magnetometer and each of the N magnetometers (i.e. each of the measuring magnetometer and the N61 magnetometers whose field cancellation system is deactivated), said determination comprising:
    - the detection of a contribution of a reference magnetic field in the measurement of the ambient magnetic field on one of the measurement axes;
    - the calculation of a ratio between the amplitude of said contribution of the reference magnetic field and the known amplitude of said reference magnetic field.

Some preferred but non-limiting aspects of this method are as follows:

said steps of the first phase are reiterated N by adopting, at each iteration, a new magnetometer of the array as a measuring magnetometer;

each reference magnetic field carries an information item which is specific thereto and the detection of a contribution of a reference magnetic field comprises the identification of the information specific to said reference magnetic field;

the information specific to a reference magnetic field is a characteristic frequency, for example a high base frequency at a power of a given number;

the magnetometers are parametric resonance magnetometers which each comprise an excitation system which is capable of being activated to induce parametric resonance excitation radiofrequency fields and, during the first phase, said excitation system of the N magnetometers is activated;

it comprises a second phase which is identical to the first phase (P1) except in that the excitation system of the N−1 magnetometers other than the measuring magnetometer is deactivated;

the second phase includes N iterations, each iteration using a different measuring magnetometer among the N magnetometers.

BRIEF DESCRIPTION OF DRAWINGS

Other aspects, aims, advantages and features of the invention will appear better on reading the following detailed description of preferred embodiments thereof, given by way of non-limiting example, and made with reference to the appended drawings in which.

DETAILED DISCLOSURE OF PARTICULAR EMBODIMENTS

The invention relates to a magnetic field measuring apparatus, more particularly an apparatus equipped with N (natural integer at least equal to two) vector magnetometers arranged in an array. This apparatus finds particular application in the medical field for the imaging of biomagnetic fields, in particular in magnetoencephalography or in magnetocardiography.

The invention relates more particularly to an apparatus configured to allow the implementation of the method for calibrating magnetometers described below. This method allows estimating the impact of the arraying of magnetometers, by measuring the disturbance that the operation of one of the magnetometers introduces to the measurement carried out by another magnetometer.

In order to apply this method, as well as more generally to be able to successfully operate an array of magnetometers in a closed loop, it is preferable that the magnetometers of this array are capable of measuring the three components of the magnetic field. Indeed, in the opposite case, a closed loop operation does not allow guaranteeing the absence of residual field in any magnetometer of the array, a necessary condition for a measurement of the couplings free from the artefacts which have been described above.

Without this being limiting to the invention, the magnetometers of the array are preferably optically pumped magnetometers, for example Hanle effect magnetometers or parametric resonance magnetometers.

Figure 1:
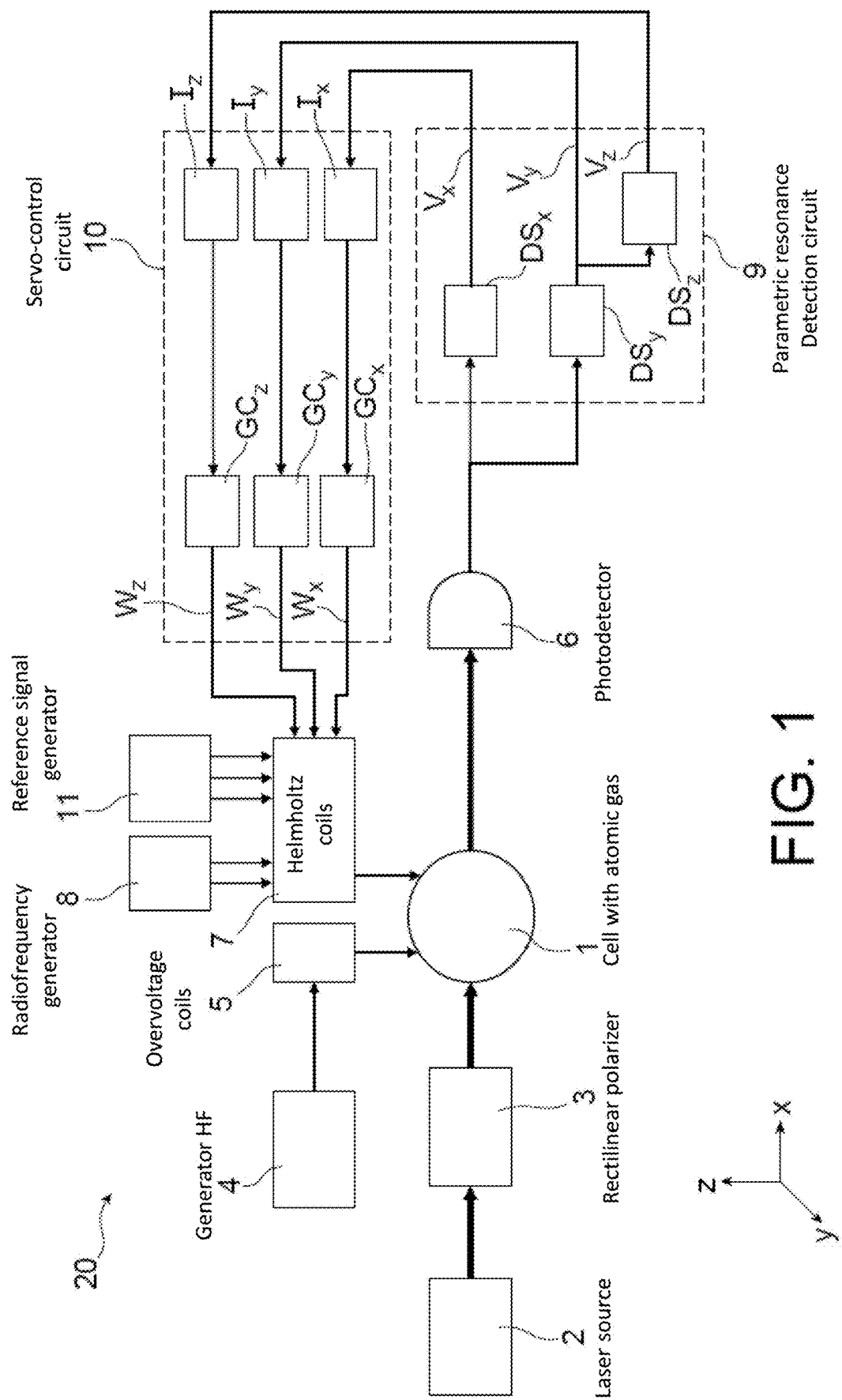
FIG. 1 is a diagram of a magnetometer belonging to an array of magnetometers according to the invention.

The following description thus takes the example of optically pumped magnetometers. With reference to FIG. 1, each of the magnetometers 20 of the array comprises a cell 1 filled with an atomic gas, for example helium-4 or an alkaline gas, subjected to an ambient magnetic field whose projection on three axes of rectangular coordinates x,y,z defines three components. The ambient magnetic field is thus broken down into three components Bx, By and Bz each according to one of the measurement axes of the magnetometer x, y and z.

The cell 1 is illuminated by an optical pumping source, made of laser source 2 and rectilinear polariser 3, arranged to emit, in the direction of the cell 1, a light beam, for example a laser beam, tuned to a pumping wavelength (this beam is thus also designated by pump beam). The pumping wavelength is wedged on an atomic transition line, for example on the line $D_0$ at 1083 nm in the case of helium-4. The light beam may be emitted by the laser source 2 and be linearly polarised by means of the rectilinear polariser 3 interposed between the laser source 2 and the cell 1 or directly integrated into the laser source 2. The light beam propagates in a direction of propagation coinciding with the x axis and is linearly polarised along the z axis.

In the case where the sensitive element is helium-4, the magnetometer 20 moreover includes a high frequency (HF) discharge system, comprising a generator HF 4 and overvoltage coils 5, to bring the atoms of the atomic gas in an energised state where they are capable of undergoing the atomic transition when they are illuminated by the light beam, typically in the metastable state $2^3S_1$.

When the magnetometer 20 is a parametric resonance magnetometer, it also comprises an excitation system capable of being activated to induce parametric resonance excitation radiofrequency fields. This parametric resonance excitation system comprises a radiofrequency generator 8 which supplies Helmholtz coils 7 with orthogonal axes which surround the cell in order to generate a parametric resonance excitation magnetic field, also referred to as an excitation radiofrequency field. This excitation circuit more particularly generates a radiofrequency magnetic field having two components orthogonal to the polarisation direction and each oscillating at its own oscillation frequency, namely a component $B_\omega \cos \omega t$ along the x axis oscillating at the pulsation $\omega$ (with for example $\omega=2\pi.3000$ kHz) and a component $B_\Omega \cos \Omega t$ along the y axis oscillating at the pulsation $\Omega$ (with for example $\Omega=2\pi.16$ kHz). These components lead to resonances at each of the oscillation frequencies $\Omega/2\pi$, $\omega/2\pi$ and to an inter-harmonic of the oscillation frequencies $(\omega\pm\Omega)/2\pi$, these resonances being associated with the values of the ambient field in the x, y and z directions respectively.

The magnetometer 20 moreover comprises a photodetector 6 arranged to receive the light beam having passed through the cell and a parametric resonance detection circuit 9 configured, when the magnetometer 20 is a parametric resonance magnetometer, to carry out a synchronous detection at a harmonic of each of the oscillation frequencies of an electrical signal delivered by the photodetector and a synchronous detection at an inter-harmonic of the oscillation frequencies of the electrical signal delivered by the photodetector. The device 9 includes three detection channels: a first channel Vx for detecting the signal at $\Omega/2\pi$ (x axis), a second channel Vy for detecting the signal at $\omega/2\pi$ (y axis), and a third channel Vz for detecting the signal at $\Omega\pm\omega/2\pi$ (z axis). The signal on each of the first and second channels Vx, Vy is first amplified then filtered with a band-pass filter corresponding to the appropriate central frequency (i.e. corresponding to that of the applied RF field). The obtained signal is then multiplied by a reference signal and processed by a synchronous detector DSx, DSy. The third channel Vz uses two synchronous detections in series, one at $\omega/2\pi$ by means of the detector DSy of the second channel Vy and the other at $\Omega/2\pi$ by means of a synchronous detector DSz.

The magnetometer 20 also comprises a field cancellation system capable of being activated to operate the magnetometer in zero field. This system may take the shape of a servo-control circuit 10 of the closed-loop magnetometer. Such a servo-control circuit comprises three servo-control channels Wx, Wy, Wz each coupled to an output of a corresponding detection channel Vx, Vy, Vz. Each of the servo-control channels Wx, Wy, Wz uses the output of the corresponding detection channel as an error signal to constantly readjust a compensation field. Each of the servo-control channels Wx, Wy, Wz comprises an integrator Ix, Iy, Iz configured to deliver a compensation signal and a current generator GCx, GCy, GCz driven by the compensation signal to inject current into one of the Helmholtz coils 7 in order to generate a compensation magnetic field BCx, BCy, BCz which is opposite to a component of the ambient field Bx, By, Bz. The measurement of the currents flowing in the coils 7 allows deducing the fields which it is necessary to apply in order to cancel the different components of the ambient field, and therefore to have the value of these various components.

The magnetometer 20 is also provided with a circuit for generating reference magnetic fields and the measuring apparatus (i.e. the array of magnetometers), for its part, includes a computer configured to drive the magnetometers of the array and determine coupling coefficients therebetween in accordance with the method which will be described later. The reference magnetic field generation circuit may comprise a reference signal generator 11 connected to each of the Helmholtz coils 7 in parallel with the circuit for connecting the coil to the generator 8 of the parameter resonance excitation system and to the servo-control circuit 10 of the closed-loop magnetometer. This connection of the reference signal generator 11 to each of the Helmholtz coils 7 may be made via a bias resistor with a value which is higher than the impedance of the coil at low frequency (<kHz). The sum of the currents on the coil then allows keeping the dynamics specific to the magnetometer unchanged, while generating the desired reference field.

Due to the arraying of magnetometers and in the usual use of this array, the magnetic field measured at a magnetometer integrates contributions from all other magnetometers. Thus, the magnetic field $B_{Gi}$ generated by a magnetometer $M_i$ (in reality by a coil of the magnetometer $M_i$) induces a field $B_{Mj}$ at a magnetometer $M_j$ (in reality on each of the measurement axes of the magnetometer $M_j$) according to a coupling coefficient $$C_{ij} = \frac{B_{M_j}}{B_{Gi}}.$$

It is sought to determine, during a calibration operation prior to a usual use of the array of magnetometers, a coupling matrix consisting of the different coupling coefficients. This matrix is of size $3N\times3N$, where N corresponds to the number of magnetometers in the array and the number 3 illustrates the three axes of the magnetometers. Thus $B_{Mj}=\Sigma_i C_{ij}\cdot B_G$, is obtained, with the indices i and j varying from 1 to 3N, each component of a field generated by a magnetometer being seen on each of the measurement axes of the magnetometers (three measurements $B_{Mj}$ are thus obtained, each integrating the contribution of each of the three fields $B_{Gi}$).

During a measurement phase subsequent to this calibration phase, it is possible, by resorting to an inversion of the coupling matrix, to go back, for each magnetometer, to the actual magnetic field, as it would be measured in the absence of the array.

The different steps of this calibration operation are described below with reference to FIG. 2. This operation uses the coils 7 of the magnetometers to generate, by means of the reference signal generator 11, magnetic fields of known amplitude. The resulting field is measured in turn by one of the magnetometers of the array, in order to establish the coupling matrix and its $3N\times3N$ coefficients.

The calibration operation comprises a first phase P1 which includes N iterations, each iteration using a different measuring magnetometer among the N magnetometers.

During each iteration of the first phase P1, the N magnetometers are separated into N−1 magnetometers whose field cancellation system is deactivated and a measuring magnetometer whose field cancellation system is activated. When the magnetometers are of the parametric resonance type, their parametric resonance excitation system is activated during this first phase. Thus, the measuring magnetometer operates in zero field and carries out a measurement of the field (the field cancellation system thereof is activated), while all others do not measure and therefore do not compensate for the field in their position (their field cancellation system is deactivated), their role being confined to generating, on the coils thereof, reference fields as well as, where appropriate, the radio frequencies corresponding to their usual operation (the parametric resonance excitation system thereof is activated).

This manner of operating with the closed-loop measuring magnetometer guarantees that the characterisation of the couplings is carried out with this measuring magnetometer operating in zero field along its three measurement axes, which avoids the appearance of numerous artefacts resulting from inter-axis effects which are detrimental to the characterisation of the couplings. Moreover, the fact that the parametric resonance excitation circuits are activated during this characterisation of the couplings allows measuring these couplings by taking into account the possible misalignments of the measurement axes resulting from the couplings between the radio-frequencies of the different magnetometers when said magnetometers are of the parametric resonance type. These misalignments are also present during the operation of the sensor array and it is therefore necessary to take them into account in the determination of the coupling matrix.

Each iteration of the first phase P1 includes the following steps:
- generation GENj, by each of the N magnetometers, of a plurality of reference magnetic fields of known amplitudes and distinct directions,
- measurement MESi, by the measuring magnetometer, of the ambient magnetic field on a plurality of measurement axes;
- determination CALCij of coupling coefficients between the measuring magnetometer and the N magnetometers, from said measurement of the ambient field and the known amplitudes of the reference fields.

During the generation step GENj, the circuit for generating reference magnetic fields of each of the N magnetometers may thus be activated in such that each of the N magnetometers generates on each of these three axes (three distinct directions) a field reference of known amplitude. And during the measuring step MESi, the measuring magnetometer measure the ambient magnetic field on each of its three measurement axes.

It may happen that the amplitude of a reference field is too high and causes undesirable effects such as Eddy currents in metal elements located in the vicinity of the array. It is then possible to decrease this amplitude, for example by an order of magnitude relative to the amplitude of the other reference fields, then to take this reduction into account when calculating the coupling coefficients.

The determination CALCij of the coupling coefficients comprises the detection of a contribution of each of the reference magnetic fields in the measurement of the ambient magnetic field on one of the measurement axes. This detection is followed, for each of the reference magnetic fields, by the calculation of the coupling coefficient in the form of a ratio between the amplitude of said contribution of the reference magnetic field and the known amplitude of said reference magnetic field. The measured coupling coefficients may, for each of the measurement axes, be normalised by the self-coupling of this axis, i.e. the ratio between the amplitude of the contribution on this axis of the reference field generated on this axis and the known amplitude of this reference field.

Given that the coupling coefficients are symmetrical (i is coupled to j in the same way that j is to i), it is possible to use the calculated coupling coefficients in both directions to identify possible problems in the calibration method or even to calculate only half of these coefficients.

During the generation step GENij, the reference magnetic field generation circuit of each of the magnetometers may generate reference fields each carrying an information item which is specific thereto (i.e. an information item specific to an axis of this magnetometer), this information being able to be identified in the measurement of the ambient magnetic field carried out on one of the axes of the measuring magnetometer in order to isolate the contribution of the reference magnetic field carrying this information.

This information specific to a reference magnetic field may be a characteristic frequency, the reference signals generated by the signal generator 11 being able for example to be composed of sinusoids located at frequencies which are specific to each axis of each magnetometer. These frequencies may for example be selected at harmonics corresponding to a high base frequency at powers of a given number, i.e. $f^{p^n}$ with f the base frequency and p said given number. Thus, if the base frequency is 1 Hz and if said given number is 2, the characteristic frequencies are frequencies of 1, 2, 4, 8, 16, 32 . . . Hz. This selection of characteristic frequencies offers the advantage that the presence of any harmonic not corresponding to a power of said given number constitutes good means of diagnosing an undesired inter-axis effect. By way of example, a first magnetometer may generate, on its x axis, a reference field $B_1 \sin(2\pi t)$, on its y axis a reference field $B_1 \sin(2\pi\ 2\ t)$ and on its z axis a reference field $B_1 \sin(2\pi\ 4\ t)$, while a second magnetometer generates on its x axis a signal $B_1 \sin(2\pi\ 8\ t)$, on its y axis a reference field $B_1 \sin(2\pi\ 16\ t)$ and on its z axis a reference field $B_1 \sin(2\pi\ 32\ t)$, etc. The detection of the contribution of a reference magnetic field in the measurement of the ambient magnetic field on one of the measurement axes of the measuring magnetometer may then comprise a synchronous detection at the characteristic frequency of this reference field.

Alternatively, this information specific to an axis of a magnetometer (to a reference field generated by this magnetometer) may correspond to the duration of high and low phases of reference signals taking the form of slots. In another variant, the reference signals form an orthogonal basis such as that used in the radio emission techniques by spectrum spreading, where each magnetometer signs its emission on one of its axes by a characteristic emission sequence in different frequency bands, these bands being included in the band of signals measurable by the magnetometers of the array.

The measurement step MESi is for example carried out sequentially on each of the axes of the measuring magnetometer, with for example a measurement which is first of all carried out along a first axis of the measuring magnetometer for a sufficiently long time to allow satisfactorily detecting the contribution of each of the reference magnetic fields in the measurement of the ambient magnetic field on this first axis, for example to distinguish reference fields having close characteristic frequencies. A time of 10 seconds thus proves to be very largely sufficient to avoid any superposition of lines when the base frequency is, as in the preceding example, 1 Hz. A similar procedure is then followed on the second axis, then on the third axis of the measuring magnetometer.

Figure 2:
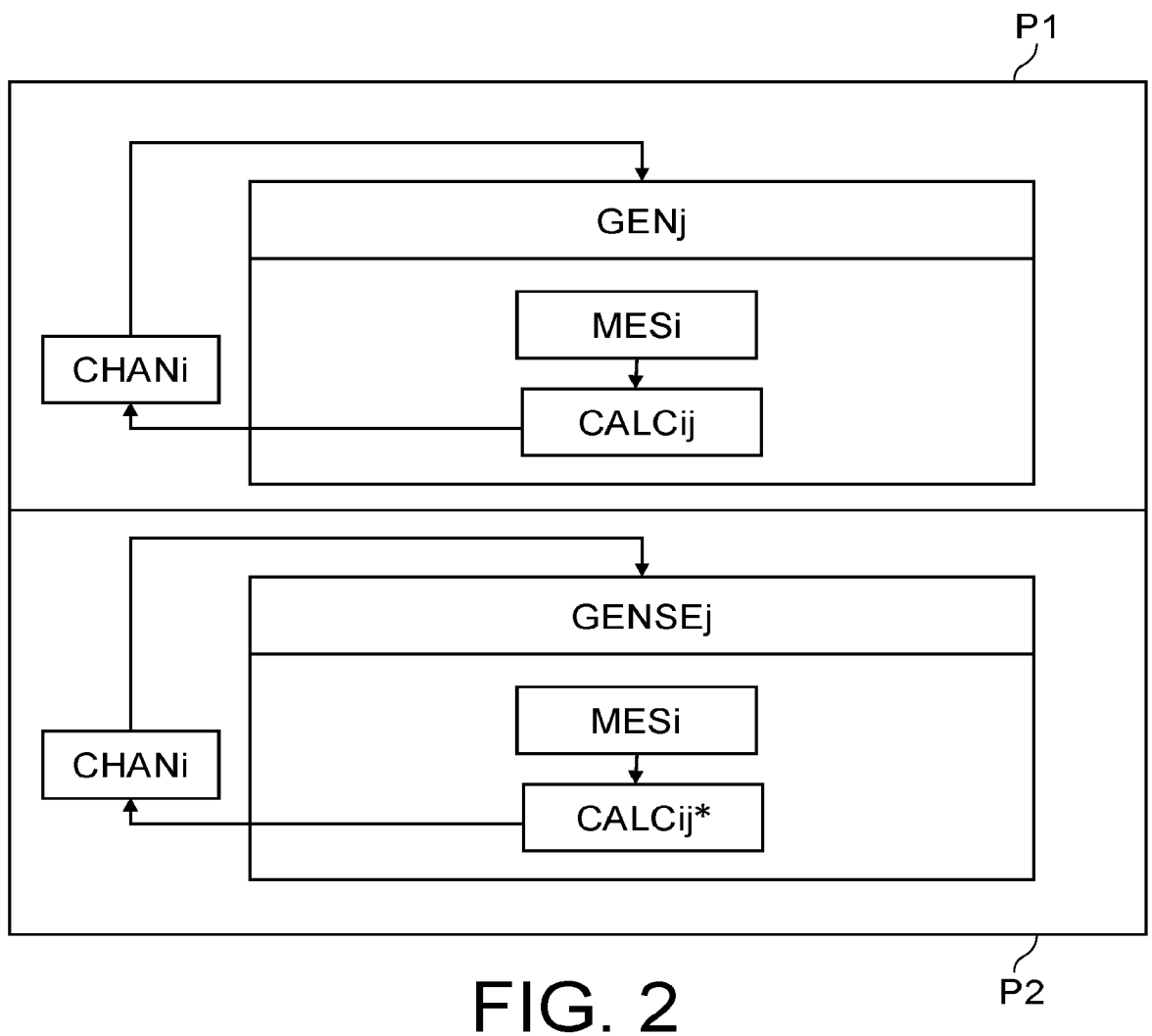
FIG. 2 is a diagram illustrating different steps of a calibration method accordance with the invention.

At the end of an iteration of the first phase, as illustrated by the block CHANi in FIG. 2, the selection of a new measuring magnetometer among the N magnetometers is carried out for a new iteration of the first phase. The previously described operations are thus reiterated so as to be carried out in total N times, each time using a different measuring magnetometer among the N magnetometers.

With reference to FIG. 2, the calibration method according to the invention may comprise a second phase P2 which also includes N iterations, each iteration using, as illustrated by the block CHANi, a different measuring magnetometer among the N magnetometers. The second phase may be implemented before or after the first phase. Alternatively, it is possible to mix iterations of the first phase and iterations of the second phase, for example by having an iteration of the first phase followed by an iteration of the second phase using the same measuring magnetometer.

It has been previously seen that activating the parametric resonance excitation radio frequencies during the first phase allows taking into account the possible misalignments of the measurement axes resulting from the couplings between the radio frequencies of the different magnetometers. However, these couplings are detrimental to the estimation of the orientations and positions of the different magnetometers of the array by a triangulation method or by other more elaborate methods such as an estimation by the least squares method taking into account the theoretical geometric configuration of the magnetic fields created by each coil of each magnetometer.

It is for this reason that for the case of a parametric resonance magnetometer, the method according to the invention may comprise a second phase P2 identical to the first phase P1 except in that, at each of its iterations, the parametric resonance excitation system of the of the N−1 magnetometers other than the measuring magnetometer is deactivated. Thus, during an iteration of the second phase, the N magnetometers are separated into N−1 magnetometers whose excitation system is deactivated and the field cancellation system is deactivated and a measuring magnetometer whose excitation system is activated and the field cancellation system is activated. With reference to FIG. 2, this second phase includes the following steps:

generation GENSEj, by each of the N magnetometers, of a plurality of reference magnetic fields of known amplitudes and distinct directions, measurement MESi, by the measuring magnetometer, of the ambient magnetic field on a plurality of measurement axes;

determination CALCij* of coupling coefficients between the measuring magnetometer and the N magnetometers, from said measurement of the ambient field and the known amplitudes of the reference fields.

The coupling matrix obtained at the end of the second phase P2 does not take into account the misalignments of the axes resulting from the coupling between the radio frequencies of the magnetometers other than the measuring magnetometer and this one. The coupling matrix determined in this second phase is only used to calibrate the positions and orientations of the different magnetometers. Thus the nine coupling coefficients between two magnetometers may be used to establish the three angles and three distances between these two magnetometers as described for example in the patent EP 3 343 240 B1. A comparison between the matrices determined by each of the first and second phases also allows measuring the misalignments of axes resulting from the radio frequency couplings.

The invention is not limited to the previously described method, but extends as previously indicated to a magnetic field measuring device configured to allow the implementation of this method. This device comprises a computer and an array of N magnetometers where each magnetometer comprises a field cancellation system capable of being activated to operate the magnetometer in zero field. The N magnetometers are in particular capable to implement the following steps while they are separated into N−1 magnetometers whose field cancellation system is deactivated and a measuring magnetometer whose field cancellation system is activated:

generation (GENj), by each of the N magnetometers, of a plurality of reference magnetic fields of known amplitudes and distinct directions, measurement (MESi), by the measuring magnetometer, of the ambient magnetic field on a plurality of measurement axes.

The computer is for its part configured in particular to detect a contribution of a reference magnetic field in the measurement of the ambient magnetic field on one of the measurement axes and to determine a coupling coefficient between the measuring magnetometer and one of the magnetometers by calculating a ratio between the amplitude of said contribution of the reference magnetic field and the known amplitude of said reference magnetic field.

The invention claimed is:

1. A method for determining a coupling between magnetometers of N magnetometers, that are formed in an array and N being ≥2, where each magnetometer comprises a field cancellation system capable of being activated to operate the magnetometer in zero field, the method being characterised in that it comprises a first phase during which one of the N magnetometers is a measuring magnetometer whose field cancellation system is activated and the other N−1 magnetometers have their field cancellation system deactivated, said first phase comprising the following steps:

generation, by each of the measuring magnetometer and the N−1 magnetometers whose field cancellation system is deactivated, of a plurality of reference magnetic fields of known amplitudes and distinct directions, measurement, by the measuring magnetometer, of the ambient magnetic field on a plurality of measurement axes; and determination of coupling coefficients between the measuring magnetometer and each of the measuring magnetometer and the N−1 magnetometers whose field cancellation system is deactivated, said determination comprising:

detection of a contribution of a reference magnetic field in the measurement of the ambient magnetic field on one of the measurement axes; and calculation of a ratio between the amplitude of said contribution of the reference magnetic field and the known amplitude of said reference magnetic field.

2. The method according to claim 1, wherein said steps of the first phase are reiterated N by adopting, at each iteration, a new magnetometer of the array as a measuring magnetometer.

3. The method according to claim 1, wherein each reference magnetic field carries an information item which is specific thereto and wherein the detection of a contribution of a reference magnetic field comprises the identification of the information specific to said reference magnetic field.

4. The method according to claim 3, wherein the information specific to a reference magnetic field is a characteristic frequency.

5. The method according to claim 4, wherein the characteristic frequency of a reference magnetic field is a high base frequency at a power of a given number.

6. The method according to claim 1, wherein the magnetometers are parametric resonance magnetometers which each comprise an excitation system which is capable of being activated to induce parametric resonance excitation radiofrequency fields and wherein, during the first phase, said excitation system of the N magnetometers is activated.

7. The method according to claim 6, further comprising a second phase which is identical to the first phase except in that the excitation system of the N−1 magnetometers other than the measuring magnetometer is deactivated.

8. The method according to claim 7, wherein the second phase includes N iterations, each iteration using a different measuring magnetometer among the N magnetometers.

9. A magnetic field measuring apparatus, comprising a computer and an array of N vector magnetometers where each magnetometer comprises a field cancellation system capable of being activated to operate the magnetometer in zero field, the N magnetometers being capable of implementing the following steps while one of the N magnetometers is a measuring magnetometer whose field cancellation system is activated and the other N−1 magnetometers have their field cancellation system deactivated:

generation, by each of the measuring magnetometer and the N−1 magnetometers whose field cancellation system is deactivated, of a plurality of reference magnetic fields of known amplitudes and distinct directions, and measurement, by the measuring magnetometer, of the ambient magnetic field on a plurality of measurement axes;

and the computer being configured to detect a contribution of a reference magnetic field in the measurement of the ambient magnetic field on one of the measurement axes and to determine a coupling coefficient between the measuring magnetometer and one of the magnetometers by calculating a ratio between the amplitude of said contribution of the reference magnetic field and the known amplitude of said reference magnetic field.

10. A method for determining a coupling between magnetometers of N magnetometers, that are formed in an array and N being ≥2, where each magnetometer comprises a field cancellation system capable of being activated to operate the magnetometer in zero field, the method being characterised in that it comprises a first phase during which one of the N magnetometers is a measuring magnetometer whose field cancellation system is activated and the other N−1 magnetometers have their field cancellation system deactivated, said first phase comprising the following steps:

generation, by only the N−1 magnetometers whose field cancellation system is deactivated, of a plurality of reference magnetic fields of known amplitudes and distinct directions, measurement, by the measuring magnetometer, of the ambient magnetic field on a plurality of measurement axes; and determination of coupling coefficients between the measuring magnetometer and each of the measuring magnetometer and the N−1 magnetometers whose field cancellation system is deactivated, said determination comprising:

detection of a contribution of a reference magnetic field in the measurement of the ambient magnetic field on one of the measurement axes; and calculation of a ratio between the amplitude of said contribution of the reference magnetic field and the known amplitude of said reference magnetic field.

* * * * *